United States Patent [19]

Possell

[11] 4,403,911
[45] Sep. 13, 1983

[54] BLADELESS PUMP AND METHOD OF USING SAME

[76] Inventor: Clarence R. Possell, 4842 Viane Way, San Diego, Calif. 92110

[21] Appl. No.: 152,998

[22] Filed: May 27, 1980

Related U.S. Application Data

[63] Continuation of Ser. No. 858,654, Dec. 8, 1977, abandoned.

[51] Int. Cl.³ ............................................. F01D 1/36
[52] U.S. Cl. .................................................. 415/90
[58] Field of Search ...................... 415/90, 1, DIG. 4

[56] References Cited

U.S. PATENT DOCUMENTS

| Re. 28,742 | 3/1976 | Rafferty et al. | 415/90 |
|---|---|---|---|
| 1,061,142 | 5/1913 | Tesla | 415/90 |
| 2,087,834 | 7/1937 | Brown et al. | 415/90 |
| 2,392,124 | 1/1946 | Denys | 415/90 |
| 2,490,066 | 12/1949 | Kollsman | 415/90 |
| 3,864,055 | 2/1975 | Kletschka et al. | 415/90 |
| 3,957,389 | 5/1976 | Rafferty et al. | 415/90 |

FOREIGN PATENT DOCUMENTS

| 405809 | 9/1943 | Italy | 415/90 |
|---|---|---|---|

*Primary Examiner*—Leonard E. Smith
*Attorney, Agent, or Firm*—William C. Babcock

[57] ABSTRACT

A bladeless pump that includes a housing that defines a circular confined space of substantial width into which either a single phase fluid or multiphase fluid is sequentially introduced through a centrally disposed inlet in a first side of the housing to be subjected to boundary layer rotational drag by at least one substantially smooth disc that rotates in the confined space intermediate the first and second side pieces of the housing and parallel thereto. The pump is capable of pumping a multiphase fluid such as that from a geothermal well that includes water, dissolved solids, steam and gas vapor, or a fluid in which the outer phase is water and the inner phase may range through such diverse materials as particled coal, marine animals such as fish, shrimp and crustaceans, and edibles that include fruits, vegetables and berries, as well as metallic objects of which steel ball bearings is an example. The pump has the capability of pumping beer without appreciably frothing the latter. Also, the pump is particularly adapted for pumping a multiphase liquid in which the inner phase is extremely frangible, of which blood is an important example. The boundary layers on the rotating discs prevent objects in the inner phase of a fluid contacting the discs and as a result there is little or no abrasion of the latter. Also, the boundary layers on the discs protect the latter from contact with bubbles in the fluid, and as a result there is no cavitation on the discs due to abrupt collapse of the bubbles.

9 Claims, 17 Drawing Figures

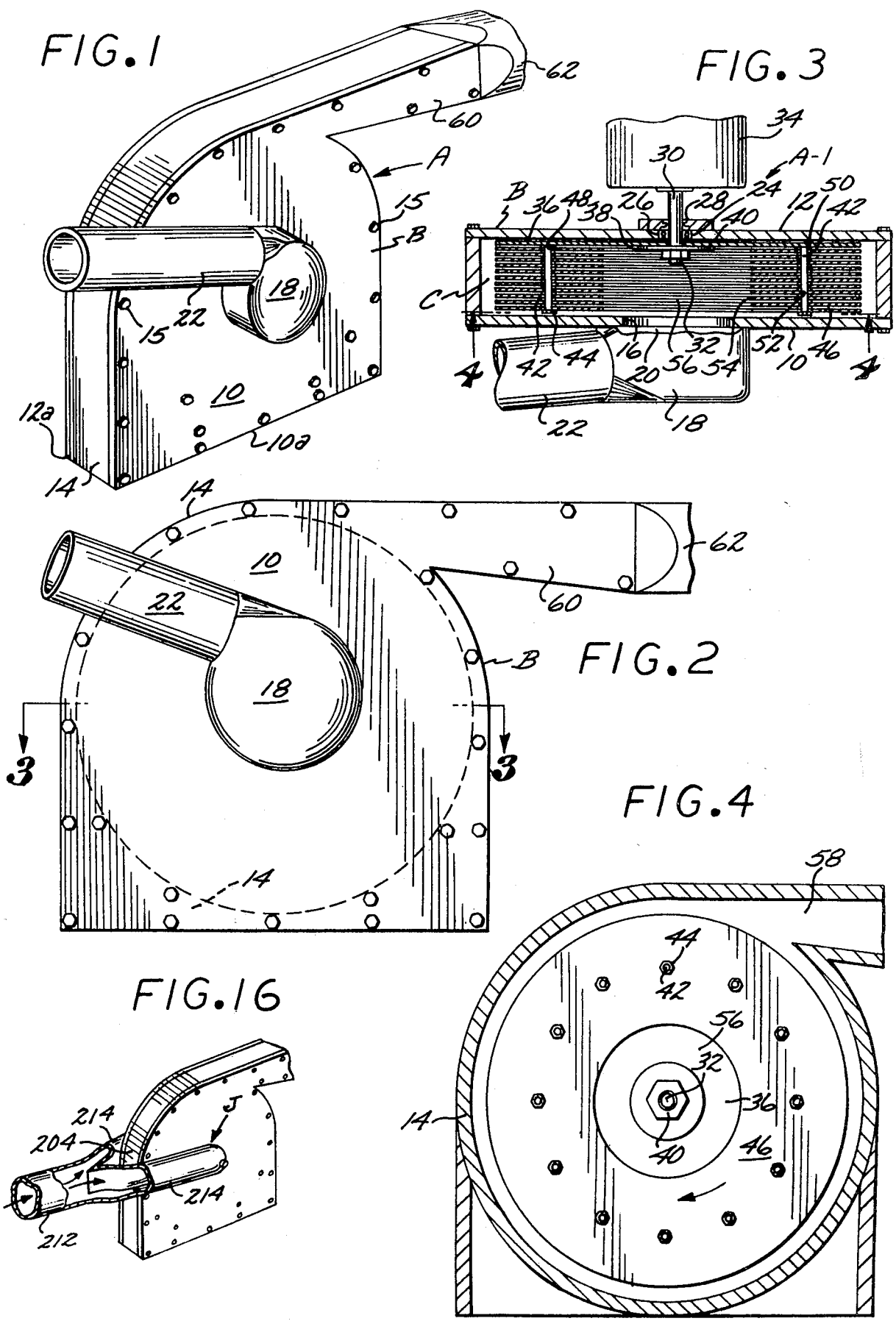

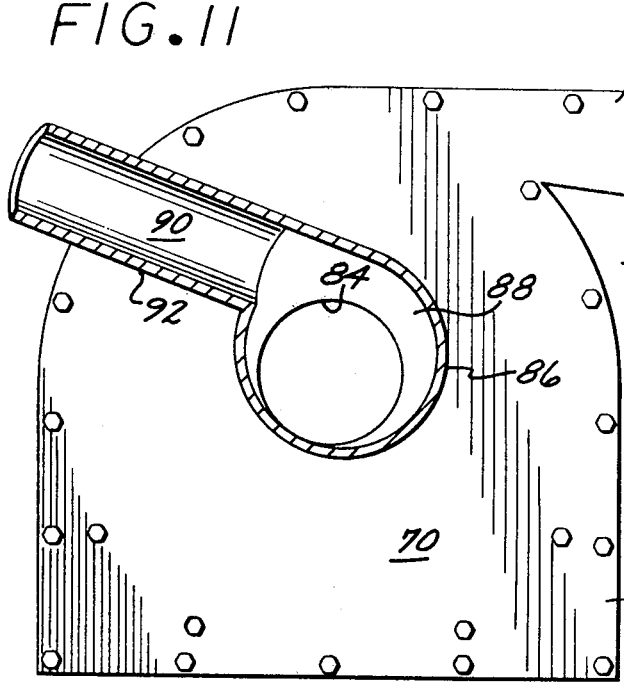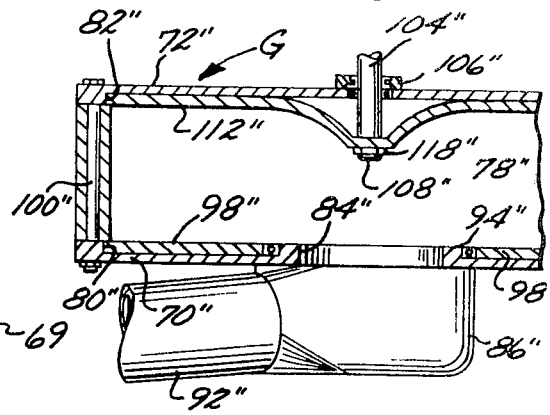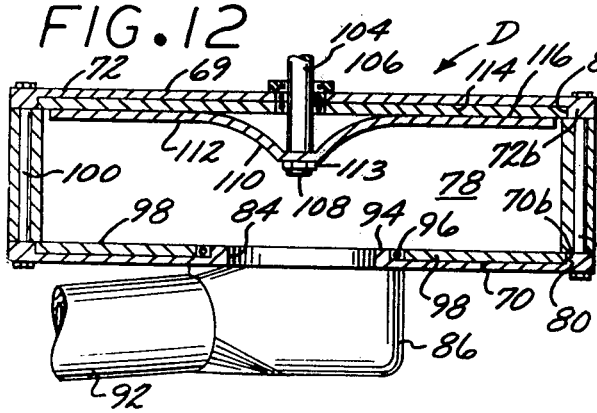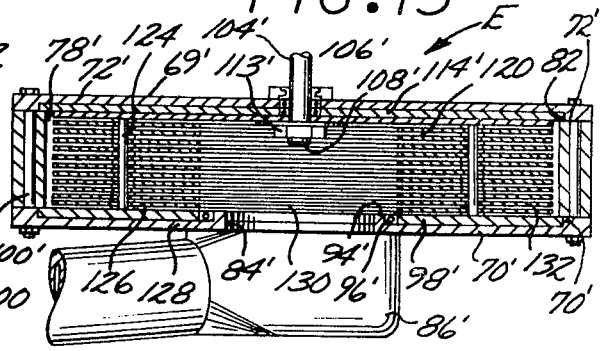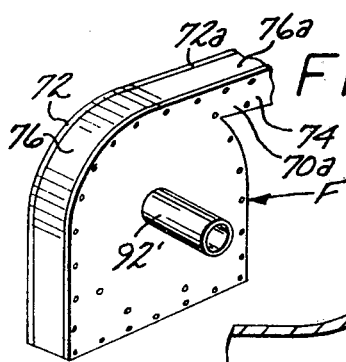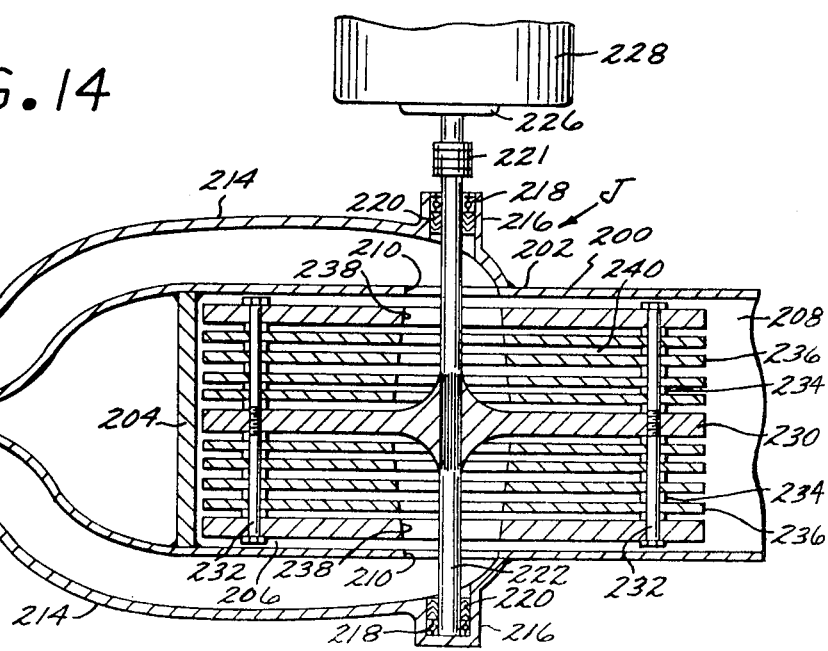

BLADELESS PUMP AND METHOD OF USING SAME

This is a continuation, division of application Ser. No. 858,654, filed Dec. 8, 1977, now abandoned.

A major object of the present invention is to provide a bladeless pump and method of using the same to transfer either a single phase fluid or multiphase fluid from a first location to a second location without damaging the material that comprises the innerphase, even when the inner phase is of an extremely frangible nature such as the red blood cells in blood.

Another object of the invention is to furnish a bladeless pump that may be used to pump such diverse materials as fruits, vegetables and berries, as well as marine animals that include fish, shrimp, crustaceans and the like from a first to a second location when the materials form the inner phase of a fluid in which the outer phase is a liquid.

Yet another object of the invention is to provide a pump that is substantially free from cavitation and erosion, and one that is capable of transferring a liquid that tends to froth from one location to a second location with a minimum of frothing.

A still further object of the invention is to supply a bladeless pump that is capable of efficiently pumping air or liquid slurries, particularly liquid slurries that have a high solids content and may contain paper, cloth, and fibrous materials such as occur in sewage, and also slurries that contained a high percentage of solids in the inner phase thereof, such as pulverized coal in coal slurry.

A still further object of the present invention is to provide a bladeless pump capable of efficiently handling hot geothermal multiphase fluids that contain water, dissolved solids in the water, steam and gas vapors.

BRIEF DESCRIPTION OF THE DRAWINGS

FIG. 1 is a perspective view of the bladeless pump;

FIG. 2 is a side elevational view of the pump shown in FIG. 1;

FIG. 3 is a transverse cross-sectional view of the pump shown in FIG. 2 taken on the line 3—3 thereon, and illustrating a first form of the pump;

FIG. 4 is a combined vertical cross-sectional and side-elevational view of the pump shown in FIG. 3, and taken on the line 4—4 thereof;

FIG. 11 is a side elevational view of the bladeless pump shown in FIG. 8 with a modified form of housing, with the fitting and first conduit being shown in section to illustrate the circular cavity in the fitting that is off-centered relative to the first opening in the first side wall to impact initial circular motion to fluid through the fitting from the first conduit prior to the fluid entering the confined space within the pump housing;

FIG. 12 is a horizontal cross-sectional view of a first modification of the pump structure shown in FIG. 8 that employs the housing illustrated in FIG. 11;

FIG. 13 is a horizontal cross-sectional view of a first modification of the pump structure shown in FIG. 3 that employs the housing structure illustrated in FIGS. 11 and 12;

FIG. 14 is a perspective view of the pump shown in FIG. 11 but modified to have the first conduit normal to the side walls thereof and centered relative to the inlet opening in the first side wall;

FIG. 15 is a horizontal cross-sectional view of a second modification of the pump structure shown in FIG. 8;

FIG. 16 is a perspective view of a second modification of the pump shown in FIG. 3; and FIG. 17 is a longitudinal cross-sectional view of the pump shown in FIG. 16 taken on the line 17—17 thereof.

DESCRIPTION OF THE PREFERRED EMBODIMENTS

Figure 5:
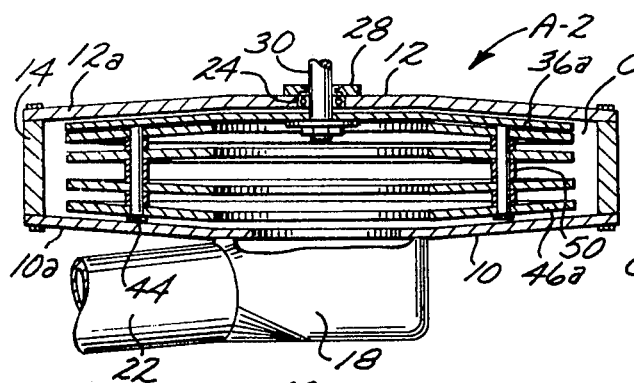
FIG. 5 is a transverse cross-sectional view of a second form of the bladeless pump.

Each of the various forms of the invention and the modifications thereof specifically identified in the above description of the drawings, include the pump housing assembly B and D shown in FIGS. 1 and 11. Pump housing assembly B includes first and second, laterally spaced side pieces 10 and 12 that are illustrated in the drawings as having lower horizontal edges 10a and 12a that are adapted to rest on or be secured to a suitable supporting surface (not shown).

The first and second side pieces 10 and 12 have a circular end piece 14 extending therebetween, which end piece is secured to the side pieces by screws 15 or other suitable fastening means. Side pieces 10 and 12 and end piece 14 cooperate to define a vertically extending, circular confined space C of substantial width.

The first side piece 10 has a first opening 16 therein that is centered relative to the circular end piece 14. A fitting 18 is in fixed sealing relationship with the exterior surface of the first side piece 10. The fitting 18 has an off centered first passage 20 defined in the interior thereof that is in communication with the first opening 10, as well as the interior of a first upwardly and outwardly extending conduit 22. The passage 20 is of such curved configuration that initial rotary motion is imparted to the fluid flowing therethrough prior to the fluid entering the confined space C. The first conduit 22 extends to a first location (not shown) at which the fluid to be pumped is stored or is available to be pumped.

A second opening 24 is formed in the second end piece 12 and is preferably coaxially aligned with the first opening 16. The second opening 24 has a bearing 28 operatively associated therewith, and the bearing supporting a shaft 30 that extends into the confined space C and is normally disposed to the second end piece 12. A seal 28 is mounted on the exterior portion of the end piece 12 and is in rotatable sealing engagement with the shaft 30.

The shaft 30 has an interiorly position shouldered end portion 32. The end portion 32 of the shaft 30 most remote from the second end piece 12 is illustrated as being driven by a prime mover 34, wuch as an electric motor or the like. A flat disc 36 is disposed within the confines of the confined space C, with the disc having a centered opening therein through which the shouldered end portion 32 of the shaft 30 extends. An apertured plate 38 is mounted on the first end portion 32 of the shaft 30, and is urged into pressure abutting contact with the central portion of the disc by a nut 40 that engages the first end 32. When the nut 40 is tightened the disc 36 is frictionally gripped between the shouldered end portion 32 and plate 38 and cannot rotate relative to the shaft.

A number of circumferentially spaced pins 42 are illustrated in FIG. 3 as projecting from the disc 36, with the pins having externally threaded free end portions adjacent the first side piece 10 that are engaged by nuts 44. A number of ring-shaped discs 46 are provided and disposed within the confined space C as shown in FIG. 3, with the ring-shaped discs having a number of circumferentially spaced openings therein that engage the pins 42. Spacers 50 are mounted on the pins 42 and situated between the ring-shaped discs 46, with the discs defining ring-shaped spaces 52 therebetween. The ring-shaped discs 46 have inner peripheries 54 that are axially aligned and cooperate to define a transverse second passage 56 as shown in FIG. 3, which second passage is in communication with the ring-shaped spaces 52 defined between the ring-shaped discs 46.

When the disc 36 and ring-shaped discs 46 are rotated concurrently by the prime mover 32 driving the shaft 30, fluid that has entered the confined space C tends to rotate therein as a circular mass. In FIG. 4 it will be seen that this circular mass of fluid rotates in a clockwise direction and as the fluid so rotates it discharges through a tangentially disposed discharge outlet 58 in the upper portion of the housing B to subsequently flow through a diverging tubular member 60 to a second conduit 62 which conduit leads to a second location (not shown) at which it is desired to pump the fluid. The tubular member 60 is illustrated in FIG. 1 as formed from extensions of the side walls 10 and 12 and end wall 14. Fluid in flowing through tubular member 60 decreases in velocity with an accompanying increase in the static pressure head thereon.

When prime mover 32 is rotating the disc 36 and the ring-shaped discs 46 concurrently as a unit, boundary layers of the fluid will adhere to the disc 36 and ring-shaped discs 46 adjacent the ring-shaped spaces 52. Such boundary layers adhere to the disc 36 and ring-shaped discs 46 and occupy substantially fixed positions thereon. These boundary layers are sheared from the balance of the fluid in the confined space C as the disc 36 and ring-shaped discs 46 rotate, and this shearing imparting sufficient rotary force to the circular body of fluid in the confined space to cause the circular body of fluid to rotate in a clockwise direction. As the fluid so rotates in the clockwise direction a portion thereon flows through the discharge outlet 58 and ultimately through the diverging member 60 and second conduit 62 to the second location (not shown). As fluid leaves the housing B as above-described, additional fluid flows into the confined space C from the first passage 20. The fluid in entering the second passage 56 has a low rotational velocity. As fluid is discharged from the outlet 58, this fluid that has entered the second passage 56 tends to flow outwardly through the spaces 52. The spaces 52 are each in width substantially greater than twice the thickness of the boundary layer of fluid on the ring-shaped discs 46 that define the ring-shaped spaces 52 to provide maximum shearing force on the outwardly moving fluid. The outwardly moving fluid is subjected concurrently to two forces, the first being a tangential shear force, and the second a centrifugal force, with the centrifugal force increasing as the fluid moves outwardly from the second recess 56. As a result of these two forces, fluid after entering the second recess 56 and discharging therefrom, pursues a spiral path prior to discharging from the discharge outlet 58.

The interior surfaces of the first and second side pieces 10 and 12, as well as the end piece 14 also have boundary layers of fluid that tend to adhere thereto, and as the circular body of fluid rotate in the confined space C, the shearing of these boundary layers from the rotating body of fluid tends to restrain the rotation of the body of fluid in the confined space. Thus, the rate at which the flat disc 36 and ring-shaped discs 46 are rotated concurrently must be at such a rate that the drag force imposed on fluid moving outwardly through the ring-shaped spaces 52 is sufficient to impart rotary motion to the body of fluid in the circular confined space and overcome the tendency of the boundary layers on the interior surfaces of the first and second side pieces 10 and 12 and end piece 14 to resist such rotary motion. In the forms of the invention shown in FIGS. 12, 13 and 15, this resisting tendency is minimized by the side surfaces that define the confined space C being free to rotate with the circular body of fluid. Under such circumstances there is a minimum differential between the rate of rotation of the circular body of fluid and the side surfaces that partially define this body of fluid.

The first form A-1 of the invention above-described is capable of being used to pump either single phase or multiphase fluid from a first location to a second location. When a multiphase fluid is being pumped in which the first phase is a liquid or gas, and the second phase a number of spaced solid objects, the spaces 52 must be of sufficient width as to allow the objects of largest cross section to move therethrough with the gaseous or liquid phase with which they are associated.

From an experience it has been found that the boundary layers of a fluid, either gaseous or a liquid, are not penetrated by solid objects entrained therewith, and as a result when a multiphase fluid is being pumped that contains solid objects, these objects will not contact the inner surface of the housing assembly B or the surfaces of the disc 36 or ring-shaped discs 46. Thus, the solid objects have minimum abrasive action on the surfaces of the pump during the passage therethrough. The pump A is also free of cavitation, for bubbles entrained with the fluid are not physically contacted by any lifting surfaces and pass between the discs. They enter the pump as bubbles and discharge from the pump as bubbles, although smaller as a result of the increased pressure at the discharge.

The second form of the invention A-2 shown in FIG. 5 is similar to the first form, other than that the disc 36 and the ring-shaped discs 46 have outer peripheral portions that taper towards one another and are identified on the drawing by the notation 36a and 46a. Due to the above-mentioned construction in the second form A-2 of the pump, the fluid will tend to remain in the spaces 52 a greater length of time, and will be subjected to rotary shear for a greater length of time, to be delivered to the discharge outlet 58 at a higher pressure than would normally be achieved when the first form A-1 of the pump is used. In FIG. 5 it will be seen that the second form A-2 of pump also has the outer peripheral portions of the first and second side pieces 10a and 12a tapering inwardly towards one another.

Figure 6:
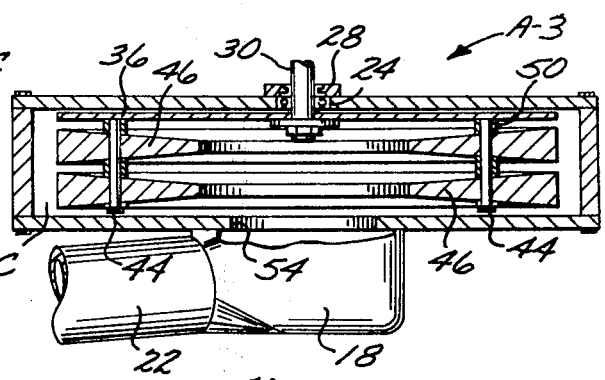
FIG. 6 is a transverse cross-sectional view of a third form of the bladeless pump.

The third form A-3 of the pump is shown in FIG. 6 differs from the first form A-1 only in that the ring-shaped discs 46 are not of uniform wall thickness, but taper outwardly from the inner periphery 54 thereof and are of maximum thickness at the outer periphery of the discs. The ring-shaped discs 46 of the above-described structure result in ring-shaped spaces 52 being defined therebetween when spacers 50 are mounted on the pins 42, which ring-shaped spaces are of maximum width adjacent inner periphery 54 and are of minimum width adjacent the outer periphery of the ring-shaped discs 46. By varying the wall thickness of the ring-shaped discs 46 as shown in FIG. 6, the rotary boundary layer drag on the fluid as it rotates as a circular body within the confined space C, may be conveniently varied, to provide fluid at the discharge outlet 58 of a desired pressure.

Figure 7:
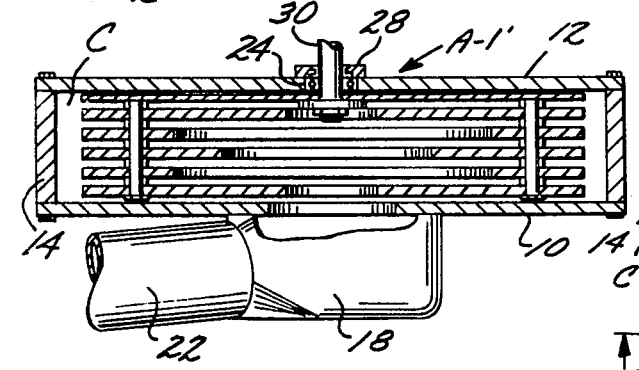
FIG. 7 is a transverse cross-sectional view of a modification of the first form of the pump.

In FIG. 7 a modification A'-1 of the first form of the invention is shown, with the modified form A'-1 varying from the first form only in that the inner peripheries 54 of the ring-shaped discs 46 vary in diameter, and this variance in diameter varying the area of the surfaces of the ring-shaped discs 46 that may impose a rotary motion to the circular body of the fluid in the confined space C, as the ring-shaped discs 46 and disc 36 rotate relative thereto.

Figure 8:
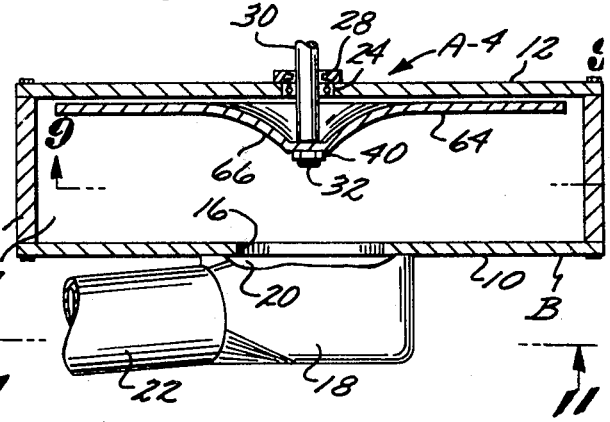
FIG. 8 is a transverse cross-sectional view of a fourth form of the bladeless pump.
Figure 9:
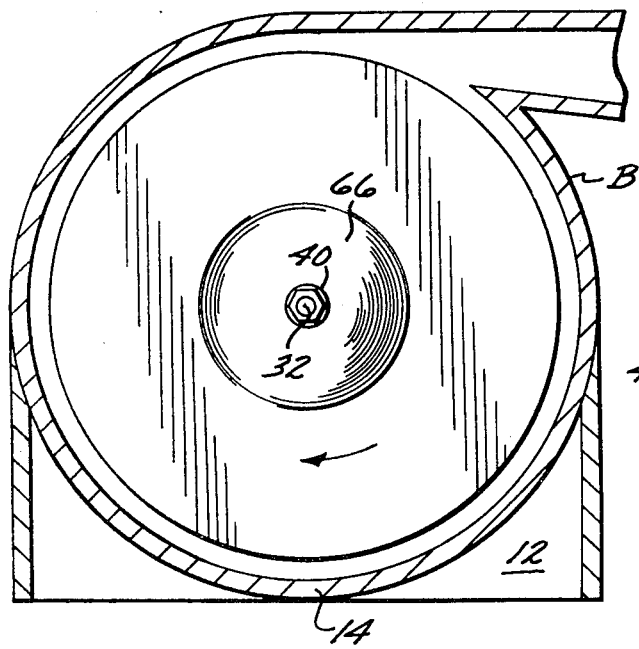
FIG. 9 is a combined vertical cross-sectional and side elevational view of the bladeless pump shown in FIG. 8, taken on the line 9—9 thereof.

The fourth form A-4 of the invention as shown in FIG. 8 differs from the first form A-1 in that the flat disc 36 and ring-shaped discs 46 are removed from the first form and replaced by a single disc 64 that has a centered hub 66 that has an opening therein that engages the shouldered end 32 of the shaft 30 and is held thereon by a nut 40. The hub 66 is illustrated in FIG. 8 as having the major portion thereof curve radially in a stream line configuration. The disc 64 as may be seen in FIG. 8 extends towards the interior surface of the second side piece 12. The fourth form A-4 of the pump is particularly adapted for use in transferring multiphase fluid from a first to a second location, such as when the first phase is a liquid, and the second phase a number of objects, such as potatoes, cherry tomatoes, fruits, vegetables, and marine animals including fish, shrimp, and the like. When the confined space C has been filled with a multiphase fluid from the first location as previously described, the prime mover 32 is actuated to cause rotation of the disc 64, and this disc when rotated in a counterclockwise direction as viewed in FIG. 9 imparting circular motion to the circular body of fluid within the confined space C. The body of fluid is rotated due to the boundary layer adhereing to the disc 64 and hub 66 being sheared therefrom by rotation of the disc, and this shearing force imparting rotary motion to the circular body of multiphase fluid in the confined space C. As the circular body of fluid in the confined space C rotates clockwise, the solid objects in the first liquid phase are subjected to increasing centrifugal force as they move outwardly relative to the hub in a generally spiral path to be ejected with the liquid first phase sequentially through the discharge outlet 58 to flow through the conduit 62 to the second location. For either single phase or multiphase fluid to discharge from the discharge outlet 58, the rate of rotation of the disc 64 and hub 66 must be sufficient as to generate a rotary shearing force on the circular body of the fluid in the confined space C as to cause the same to rotate, and overcome the shearing of the boundary layers on the interior surfaces of the first and second side pieces 10 and 12 and end piece 14 that tend to resist such rotation.

Figure 10:
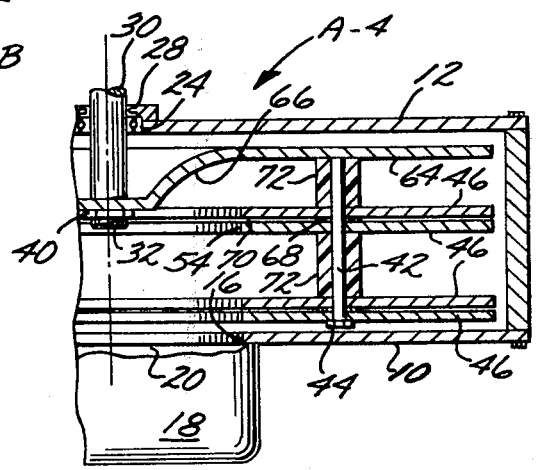
FIG. 10 is a fragmentary transverse cross-sectional view of a modification of the fourth form of bladeless pump.

A modification A'-4 of the fourth form of the invention is shown in FIG. 10, which includes a number of circumferentially spaced pins 42 that project from the disc 64 towards the first end piece 10, with the pins engaging pairs of ring-shaped discs 46. The ring-shaped discs 46 in each pair are separated by a spacer 68 mounted on one of the pins 42, and the spacer resulting in each pair of ring-shaped discs having a ring-shaped space 70 defined therebetween through which fluid may discharge outwardly towards the end piece 14 as the disc 64 and ring-shaped discs 46 rotate in unison. The pairs of ring-shaped discs 46 are separated from the disc 64 and from one another by spacers 72 mounted on the pins 42, and these spacers being of a soft resilient material such as rubber or the like. As the fluid flows into the confined space C through the first opening 16, the fluid whether single phase or multiphase is subjected to rotary motion by rotation of the disc 64 and the pairs of adjacently disposed ring-shaped discs 46. This rotary motion occurs due to the shearing of the boundary layer on the disc 64, and on the ring-shaped discs 46, from the balance of the circular body of fluid in the confined space C, and this shearing imparting rotary motion to the circular body of fluid to cause the same to be ejected from the discharge opening 58 as previously described. The spacing between the disc 64 and the pairs of ring-shaped discs 46 must be sufficiently great that the largest of the solids entrained with the fluid are able to pass radially therethrough as they describe substantially spiral paths prior to being ejected from the discharge opening 58. The spaces 70 between the pairs of spaced ring-shaped discs 46 provide additional surfaces on the ring-shaped discs 46 that have boundary layers thereon that are sheared from the balance of the circular body of fluid, and increase the circular drag on the circular body of fluid as the disc 64 and pairs of ring-shaped discs 46 rotate relative thereto. Due to the increased areas that have boundary layers thereon that rotate relative the circular body of fluid, the drag force imposed on the circular body of fluid will be sufficiently great as to overcome the resistance drag force imposed by boundary layers on the interior surfaces of the first and second side pieces and end piece 14. As a result fluid entering the confined space C may be caused to rotate when the shaft 30 is rotated at a relatively slow speed. The spacers 72 serve a dual function, not only of maintaining the pairs of ring-shaped discs 46 in laterally spaced relationship with one another, but preventing damage to frangible objects entrained with a liquid or gas as the object and liquid are caused to flow through the modified form A'-4 of the fourth form of the invention to discharge to the second location through the second conduit 62.

The pump D illustrated in FIGS. 11 and 12 is a first modification of the bladeless pump illustrated in FIG. 8 and has a housing 69 that includes first and second laterally spaced side walls 70 and 72 that have extensions 70a and 72a that partially define the diverging outlet structure 74 as shown in FIG. 14. An end wall 76 is disposed between the first and second side walls and cooperates therewith to define a circular confined space 78 of substantial width. The end wall 76 has spaced extensions 76a that cooperate with the extensions 70a and 72a to define the diverging outlet structure 74.

The first and second side walls 70 and 72 on the adjacent faces thereof have circular ribs 70b and 72b that project towards one another and are in abutting sealing contact with oppositely disposed side surfaces of end piece 76. The end piece 76 as may be seen in FIG. 12 is of greater thickness than the depth of the ribs 70b and 72b and cooperates with the ribs to define first and second circular recesses 80 and 82 shown in FIG. 12.

First side wall 70 has a centered first opening 84 therein that serves as a fluid inlet. A fluid conducting fitting 86 is secured to the exterior surface of first side wall 70 as illustrated in FIGS. 11 and 12. The fitting defines a generally circular cavity 88 within the interior thereof that is of substantially greater diameter than the first centered opening 84 in first side wall 70, which first opening serves as a fluid inlet. Cavity 88 and first opening 84 are in communication but off centered relative to one another. Cavity 88 is also in communication with a longitudinal passage 90 in a first conduit 92 that extends to a first location (not shown) where the fluid to be pumped is situated. The passage 90 is tangentially disposed relative to cavity 88. Fluid entering the cavity 88 from passage 90 has initial rotary motion imparted thereto prior to discharging into confined space 78 through the first opening 84. The first side wall 70 has a ring-shaped boss 94 projecting inwardly from the interior surface thereof as shown in FIG. 12, which boss surrounds first opening 84. Boss 94 supports a bearing 96 that in turn rotatably supports a first circular plate 98 that has the circumferential edge portion slidably and rotatably disposed in first circular recess 82. Ribs 70b, 72b and end piece 76 have spaced transverse bores (not shown) therein through which bolts 100 extend that hold the housing together as an integral unit.

Second side wall 72 has a second opening 102 threin that is preferably axially aligned with first opening 84. A power driven shaft 104 extends into confined space 78 through second opening 102, and is rotatably supported by a bearing and seal 106 that is preferably secured to the exterior surface of second side wall 72. The shaft 104 has an externally threaded shouldered end portion 108 situated within confined space 78 that extends through an opening (not shown) in the hub portion 110 of a disc 112 that has a diameter less than that of the confined space 78. A nut 113 engages threaded end portion 108 and serves to removably secure disc 112 thereto.

A second circular plate 114 is rotatably supported on shaft 104 and is disposed between disc 112 and the interior surface of the second side wall 72. Second plate 114 is of such diameter that the peripheral edge portion thereof is rotatably disposed in the second circular recess 82.

When driven shaft 104 rotates, disc 112 rotates concurrently therewith. Fluid that has initial rotation imparted thereto in fitting 86 flows into confined space 78 and due to rotational drag imparted thereto by disc 112 rotates in the confined space 78 is subjectd to a minimum restraining force in the housing 69 as the first and second plates 98 and 114 are free to rotate therewith. The fluid as it rotates in confined space 78 sequentially flows through the diverging discharge structure 74 to a second conduit 115 that leads to a second location (not shown) to which it is desired to transfer the fluid. Shaft 104 is maintained by conventional means (not shown) at a fixed position relative to housing 69. The disc 112 is separated from second plate 114 by a space 116.

The pump E illustrated in FIG. 13 employs the assembly of elements common to the pump D, but with the disc 112 being replaced by a rotor assembly 120. Elements of the pump E common to the pump D illustrated in FIG. 12 are identified by the numerals previously used but with primes being added thereto.

The disc 112 of pump D is replaced by a flat first disc 122 in pump E that forms a part of rotor assembly 120. Disc 122 has a number of circumferentially spaced pins 124 projecting therefrom that extend towards first side wall 98'. The pins 124 serve to support a number of second discs 126 thereon which discs are of ring-shape and are held in spaced relationship with one another in the same manner as described in detail with the pump illustrated in FIG. 3. The inner peripheries 128 of the second discs 126 define a second transverse passage 130 that is in communication with ring-shaped spaces 132 formed between the second discs 126. The second pump E operates in the same manner as the pump illustrated in FIG. 3, but requires less power to operate as the first and second plates 98' and 114' are free to rotate with the rotating body of fluid in the confined space 78'. Thus, as the body of fluid rotates in the confined space 78' there is a minimum in the differential in the rate of rotation of the body of fluid and the side plates 98' and 114'.

The pump F shown in FIG. 14 is of the same internal structure as pump D illustrated in FIG. 11, and differs from pump D in that fitting 86 is eliminated, with first conduit 92 being disposed normal to the pump housing and in direct communication with first opening 84.

The pump G shown in FIG. 15 is of the same general structure as the pump D, and differs from the latter by having the second plate 114 omitted, and the disc 112" of such diameter that the peripheral portion thereof is rotatably disposed in second recess 82". Elements in pump G common to pump D are identified on the drawings by the same numerals previously used but with double primes being added thereto. Pump G operates in the same manner as pump D illustrated in FIG. 12. Pumps D and G are particularly adapted for pumping multiphase fluids in which the inner phase has a high content of solids and may contain pieces of paper, rags and other fibrous or stringy materials. Such materials have no adverse effect on the operation of these pumps.

The pumps D and G are useful in transferring objects, either animate or inanimate from a first location to a second location. The objects are mixed with fluid at a first location to provide a multiphase fluid in which the outer phase is fluid and the inner phase the objects. The objects may have such diverse physical characteristics as those common to vegetables, fruits and berries, as well as to fish, shrimp, crustaceans and the like, as well as to granular materials such as powdered coal. The multiphase fluid may also be either a liquid or air slurry, raw or partially treated sewage and the like.

The pump J illustrated in FIGS. 16 and 17 includes a housing 200 that is defined by two laterally spaced side pieces 202 and an arcuate end piece 204 that extends therebetween to define a circular confined space 206. The end piece 206 has extensions projecting therefrom that cooperate with extensions of the side pieces 204 to define a fluid discharge 208 that is preferably of diverging configuration. The side piece 202 have transversely aligned fluid inlet openings 210 therein as may best be seen in FIG. 17.

Fluid may flow from a source (not shown) through a conduit 212, which conduit develops adjacent the pump J into a pair of conduit extensions 214 of lesser transverse cross-section that are in communication with the inlet openings 210. The conduit extensions 214 have laterally spaced bosses 216 projecting outwardly therefrom, with the bosses being axially aligned and centered relative to the inlet opening 210. Each boss supports a bearing 218 and a low pressure seal 220, both of which may be of conventional present day design.

The bearings 220 rotatably support a shaft 222 that is in sealing engagement with the seals 220, and the shaft extending transversely across confined space 206. Shaft 222 by a coupling 224 is connected to the drive shaft 226 of a prime mover 228, preferably an electric motor.

Shaft 222 at the center of confined space 206 has a circular plate 230 of substantial strength secured thereto. A number of elongate, circumferentially spaced rigid members 232 extend outwardly equal distances from opposite sides of the plate, which members may be bolts or the like. The members 232 in cooperation with spacers 234 mounted thereon serve to support two sets of ring-shaped discs 236 on opposite sides of the plate 230. The ring-shaped discs 236 have axially aligned centered opening 238 therein. The ring-shaped discs 236 in each set are separated by spaces 240.

When prime mover 228 is operating, the plate 230 and the two sets of ring-shaped discs 236 are rotated concurrently. Fluid is drawn into the confined space 206 through inlet openings 210 at the same rate and exerts oppositely directed forces on the plate 230, and as a result the shaft 222 has no appreciable longitudinal thrust exerted thereon. The fluid after entering confined space 206 is discharged therefrom through fluid discharge 208 in the same manner as in pump A-1 shown in FIG. 3.

The bladeless pumps have been described previously in detal as to structure and the method of using the same and need not be repeated.

What is claimed is:

1. A pump for use in transferring either a single phase or multiphase fluid from a first location to a second location which includes:
   a. a housing assembly that includes first and second vertically disposed, laterally spaced first and second side walls and a continuous end wall that extends transversely therebetween to cooperate therewith to define a circular confined space, a centrally disposed first opening in said first side wall in communication with said first location, a discharge opening in said end wall that is at a higher elevation than said first opening and is in communication with said second location, and a second opening in said second side wall that is oppositely disposed from said first opening, said housing assembly formed from a rigid material resistant to action by said fluid;
   b. a rotatable drive shaft that has first and second ends;
   c. bearing and seal means supported in a fixed relationship from said second side wall and coaxially aligned with said second opening therein, said bearing and seal means rotatably supporting said drive shaft, with said first end of the latter disposed within said confined space and adjacent the latter;
   d. a substantially smooth first circular disc in said confined space secured to said first end of said drive shaft and intermediately positioned between said first and second side walls with said second end of drive shaft when rotated at greater than a first rate causing a circular body of said fluid in said confined space to rotate due to a rotary force exerted on said body of fluid as a boundary layer of said fluid on the exterior surface of said first circular disc is rotated relative to said body of water to be sheared therefrom, and said fluid entering said confined space through said first opening having increasing rotary velocity imparted thereto to sequentially move outwardly in a spiral path due to the centrifugal force imposed thereon and be sequentially ejected from said discharge opening to flow to said second location said first side wall and end wall at their junction defining a circumferentially extending recess that is in communication with said confined space; and
   e. a first ring-shaped side plate rotatably supported in said confined space adjacent said first side wall, and said first side plate having the outer peripheral edge portion thereof rotatably supported in said recess, said first side plate including a centered opening axially aligned with said first opening in said first side wall, with said first side plate free to rotate with said circular body of liquid to minimize the frictional drag on said circular body of fluid as said circular body rotates relative to said housing.

2. A pump for use in transferring either a single phase or multiphase fluid from a first location to a second location which includes:
   a. a housing assembly that includes first and second vertically disposed, laterally spaced first and second side walls and a continuous end wall that extends transversely therebetween to cooperate therewith to define a circular confined space, a centrally disposed first opening in said first side wall in communication with said first location, a discharge opening in said end wall that is at a higher elevation than said first opening and is in communication with said second location, and a second opening in said second side wall that is oppositely disposed from said first opening, said housing assembly formed from a rigid material resistant to action by said fluid; said first side wall and end wall at the junction thereof defining a circumferentially extending first recess that is in communication with said confined space; and
   b. a first ring-shaped side plate rotatably supported in said confined space adjacent said first side wall, and said first side plate having the outer peripheral edge portion thereof rotatably supported in said recess, said first side plate including a centered opening axially aligned with said first opening in said first side wall, with said first side plate free to rotate with said fluid to minimize the frictional drag on said fluid as said fluid rotates relative to said housing.

3. A pump for use in transferring either a single phase or multi-phase fluid from a first location to a second location which includes:
   a. a housing assembly that includes first and second vertically disposed, laterally spaced first and second side walls and a continuous end wall that extends transversely therebetween to cooperate therewith to define a circular confined space, a centrally disposed first opening in said first side wall in communication with said first location, a discharge opening in said end wall that is at a higher elevation than said first opening and is in communication with said second location, and a second opening in said second side wall that is oppositely disposed from said first opening, said housing assembly formed from a rigid material resistant to action by said fluid, said second side wall and end wall at their junction defining a circumferentially extending recess;
b. a power driven drive shaft that has first and second ends;
c. bearing and sealing means supported in a fixed relationship with said second side wall and coaxially aligned with said second openign therein, said bearing and sealing means rotatably supporting said power driven shaft with said first end thereof adjacent said confined space; and
d. a substantially smooth circular disc secured to said first end of said shaft and disposed in said confined space with the periphery of said disc disposed in said recess, said disc when rotated at greater than a first rate causing a circular body of said fluid in said confined space to rotate due to a rotary force exerted on said body of fluid as a boundary layer of said fluid on the exterior surface of said disc is rotated relative to said body of fluid to be sheared therefrom, with said fluid entering said confined space through said first opening having increased rotary velocity imparted thereto to sequentially move outwardly in a spiral path due to the centrifugal force imposed thereon and be sequentially ejected from said discharge opening to flow to said second location, and said pump not clogging when said multiphase fluid has an outer liquid phase and an inner phase that includes solids such as stringy material, pieces of paper, rags and the like.

4. A method of concurrently pumping a liquid and a plurality of entrained solid objects that may be of a fragile nature from a first location to a second location without damage to said objects, said method comprising the steps of:
a. defining a first vertical circular confined space at an elevation less than that of said first location;
b. allowing said liquid and entrained objects to flow downwardly by gravity from said first location to said first confined space to enter the latter tangentially and have the kinetic energy of said liquid and entrained objects impart rotary motion to said liquid and entrained objects in said first confined space;
c. defining a second vertical circular confined space adjacent said first confined space, said second space having first and second side surfaces that are parallel and laterally spaced from one another;
d. discharging said rotating liquid and objects from said first confined space into said second confined space through a centered opening in said first side surface;
e. rotating a circular plate in said second confined space adjacent said second side surface at a sufficiently rapid rate as to accelerate the rate of rotation of said liquid and objects entering said second confined space to the extent said liquid and objects rotate in said second confined space as a circular body, and said objects due to the centrifugal force imposed thereon tending to move outwardly in said circular body in a spiral path;
tangentially discharging said liquid and objects from an outer portion of said second confined space through a diverging passage to decrease the velocity of said liquid and increase the static head thereon; (and)
g. directing said liquid and objects from said diverging passage to said second location, with the lateral spacing between said first side surface and said plate, said opening in said first side surface, and said diverging passage being sufficiently great as to permit the free passage of the largest of said objects therethrough; and
h. allowing said first side surface to rotate freely with said body of liquid in said second confined space to minimize frictional resistance of said body of liquid as it rotates relative to said first side surface.

5. The method as defined in claim 4 in which said second side surface is allowed free to rotate freely with said body of liquid in said second confined space to minimize frictional resistance of said body of liquid as it rotates relative to said second side surface.

6. A method as defined in claim 4 in which said liquid is water and said solid objects are selected from the class consisting of vegetables, fruits and berries that are not only transported between said first and second locations but washed during said transportation.

7. A method as defined in claim 4 in which said liquid is water and said solid objects are selected from the class that comprises live fish, shrimp, crustaceans and marine animals that are not only transported between said first and second locations but maintained in a water environment in which they can live during said transportation.

8. A method as defined in claim 4 in which said liquid is hot water and said entrained objects are bubbles of steam.

9. A method as defined in claim 4 in which said entrained objects are bubbles of gas that tend to escape from said liquid.

* * * * *